(12) United States Patent
Samuels et al.

(10) Patent No.: US 7,384,396 B2
(45) Date of Patent: Jun. 10, 2008

(54) SYSTEM AND METHOD FOR CONTINUOUS ANALYTE MONITORING

(75) Inventors: Mark A. Samuels, Norcross, GA (US); Jonathan A. Eppstein, Atlanta, GA (US); Michael R. Hatch, Sugar Hill, GA (US); Alan Smith, Atlanta, GA (US); Mark Faupel, Alpharetta, GA (US)

(73) Assignee: SpectRx Inc., Norcross, GA (US)

( * ) Notice: Subject to any disclaimer, the term of this patent is extended or adjusted under 35 U.S.C. 154(b) by 636 days.

(21) Appl. No.: 10/435,221

(22) Filed: May 8, 2003

(65) Prior Publication Data

US 2003/0191376 A1 Oct. 9, 2003

Related U.S. Application Data

(63) Continuation of application No. 09/357,471, filed on Jul. 20, 1999, now abandoned.

(60) Provisional application No. 60/093,534, filed on Jul. 21, 1998, provisional application No. 60/140,285, filed on Jun. 18, 1999, provisional application No. 60/140,252, filed on Jun. 18, 1999.

(51) Int. Cl.
*A61B 5/00* (2006.01)
(52) U.S. Cl. .................... 600/309; 600/310; 600/322
(58) Field of Classification Search .............. 600/309, 600/322, 361, 583
See application file for complete search history.

(56) References Cited

U.S. PATENT DOCUMENTS

| | | | |
|---|---|---|---|
| 2,114,599 A * | 4/1938 | Jones | 424/65 |
| 3,847,138 A | 11/1974 | Gollub | |
| 3,912,457 A | 10/1975 | Ogawa et al. | |
| 3,992,158 A | 11/1976 | Przybylowicz et al. | |
| 4,050,898 A | 9/1977 | Goffe et al. | |

(Continued)

FOREIGN PATENT DOCUMENTS

EP 0 595 237 A1 5/1993

(Continued)

OTHER PUBLICATIONS

PCT International Search Report, International Application No. PCT/99/16378, mailed Oct. 28, 1999.

(Continued)

*Primary Examiner*—Eric Winakur
*Assistant Examiner*—Etsub D Berhanu
(74) *Attorney, Agent, or Firm*—Altera Law Group, LLC

(57) ABSTRACT

A system and method for extracting a biological fluid from an organism and continuously monitoring its characteristics. The system includes a tissue interface device suitable for positioning on or about the surface of the biological membrane of the organism and a monitor and control unit coupled to the tissue interface device. The tissue interface device includes a sensor positioned in a flow path of the fluid for continuously sensing a characteristic of the biological fluid as it flows out from the one or more artificial openings formed in the biological membrane. The sensor generates a sensor signal representative thereof. The monitor and control unit electrically or optically reads the sensor to obtain a measurement of a characteristic, such as concentration of a particular analyte, of the biological fluid on a continuous basis.

20 Claims, 8 Drawing Sheets

U.S. PATENT DOCUMENTS

| | | | |
|---|---|---|---|
| 4,053,381 A | 10/1977 | Hamblen et al. | |
| 4,109,505 A * | 8/1978 | Clark et al. | 73/1.02 |
| 4,151,845 A | 5/1979 | Clemens | |
| 4,409,966 A | 10/1983 | Lambrecht | |
| 4,494,950 A | 1/1985 | Fischell | |
| 4,515,584 A | 5/1985 | Abe et al. | |
| 4,636,144 A | 1/1987 | Abe et al. | |
| 4,774,192 A | 9/1988 | Terminiello et al. | |
| 4,839,296 A | 6/1989 | Kennedy et al. | |
| 4,935,105 A | 6/1990 | Churchouse | |
| 5,203,327 A * | 4/1993 | Schoendorfer et al. | 600/362 |
| 5,271,895 A | 12/1993 | McCroskey et al. | |
| 5,362,307 A | 11/1994 | Guy et al. | |
| 5,411,647 A | 5/1995 | Johnson et al. | |
| 5,458,140 A | 10/1995 | Eppstein et al. | |
| 5,507,288 A | 4/1996 | Bocker et al. | |
| 5,569,186 A | 10/1996 | Lord et al. | |
| 5,582,184 A | 12/1996 | Erickson et al. | |
| 5,640,954 A | 6/1997 | Pfeiffer et al. | |
| 5,682,233 A | 10/1997 | Brinda | |
| 5,697,899 A | 12/1997 | Hillman et al. | |
| 5,724,966 A * | 3/1998 | Lundback | 600/372 |
| 5,746,217 A | 5/1998 | Erickson et al. | |
| 5,820,570 A | 10/1998 | Erickson et al. | |
| 5,885,211 A | 3/1999 | Eppstein et al. | |
| 5,947,921 A | 9/1999 | Johnson et al. | |
| 6,023,639 A * | 2/2000 | Hakky et al. | 604/20 |
| 6,058,321 A * | 5/2000 | Swayze et al. | 600/310 |
| 6,144,869 A * | 11/2000 | Berner et al. | 600/347 |
| 6,352,506 B1 | 3/2002 | Eppstein et al. | |
| 7,037,277 B1 | 5/2006 | Smith et al. | |

FOREIGN PATENT DOCUMENTS

| | | |
|---|---|---|
| GB | 1498332 | 1/1978 |
| WO | WO 94/06019 | 3/1994 |
| WO | WO 94/09713 | 5/1994 |
| WO | WO 94/14062 | 6/1994 |
| WO | WO 96/00110 | 1/1996 |
| WO | WO 97/04832 | 2/1997 |
| WO | WO 97/07734 | 3/1997 |
| WO | WO 97/12242 | 4/1997 |
| WO | WO 97/38126 | 10/1997 |
| WO | WO 97/42882 | 11/1997 |
| WO | WO 97/42883 | 11/1997 |
| WO | WO 97/42885 | 11/1997 |
| WO | WO 97/42886 | 11/1997 |
| WO | WO 97/42888 | 11/1997 |
| WO | WO 97/43962 | 11/1997 |
| WO | WO 98/00193 | 1/1998 |
| WO | WO 99/44508 | 9/1999 |
| WO | WO 00/19887 | 4/2000 |

OTHER PUBLICATIONS

"Ultraviolet-Laser Ablation of Skin", Lane et al., 121 Arch. Dermatol., 609-617 (1985).

"Controlled Removal to Human Stratum Corneum by Pulsed Laser", Jacques et al., 88 J. Invest. Dermatol., 88-93 (1987).

* cited by examiner

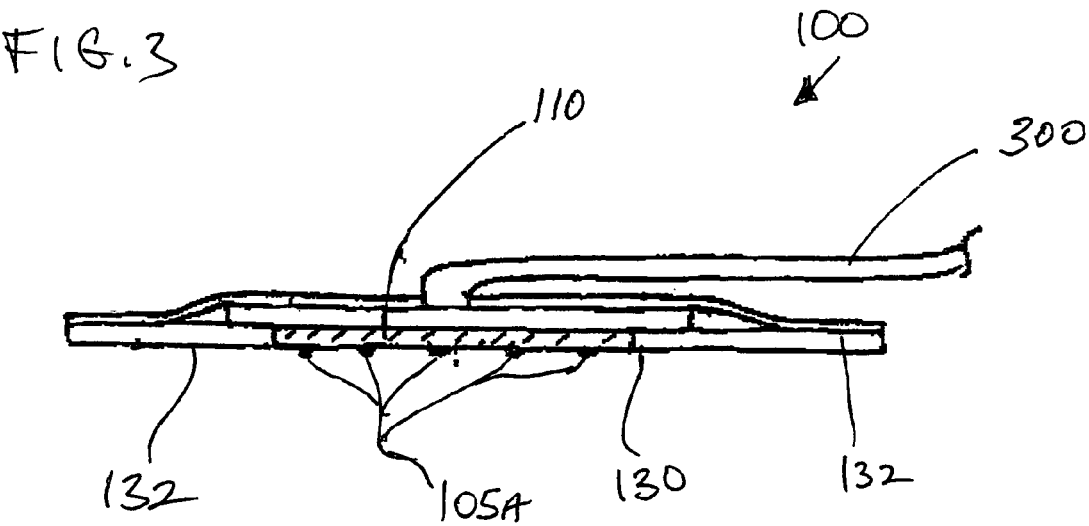
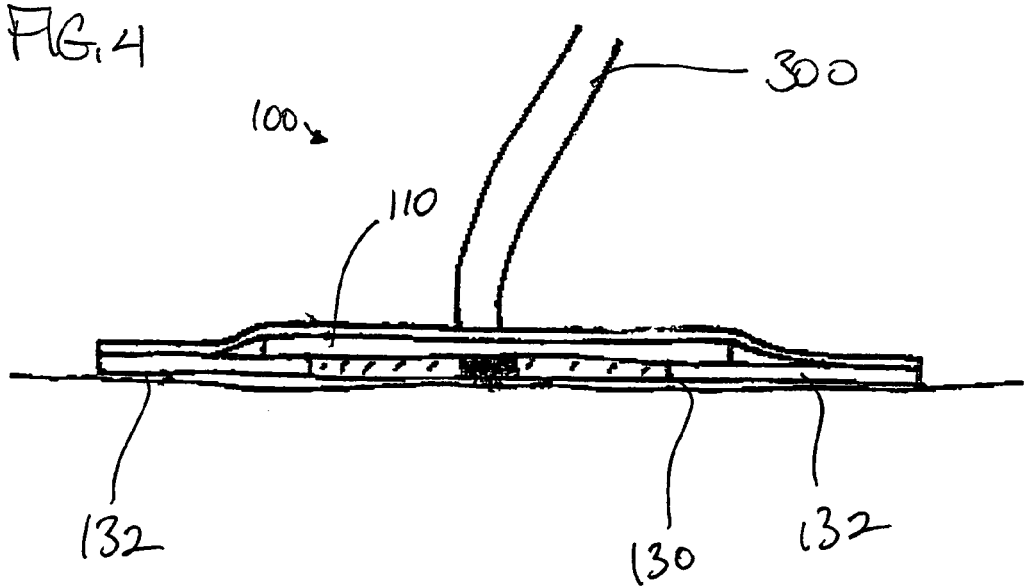

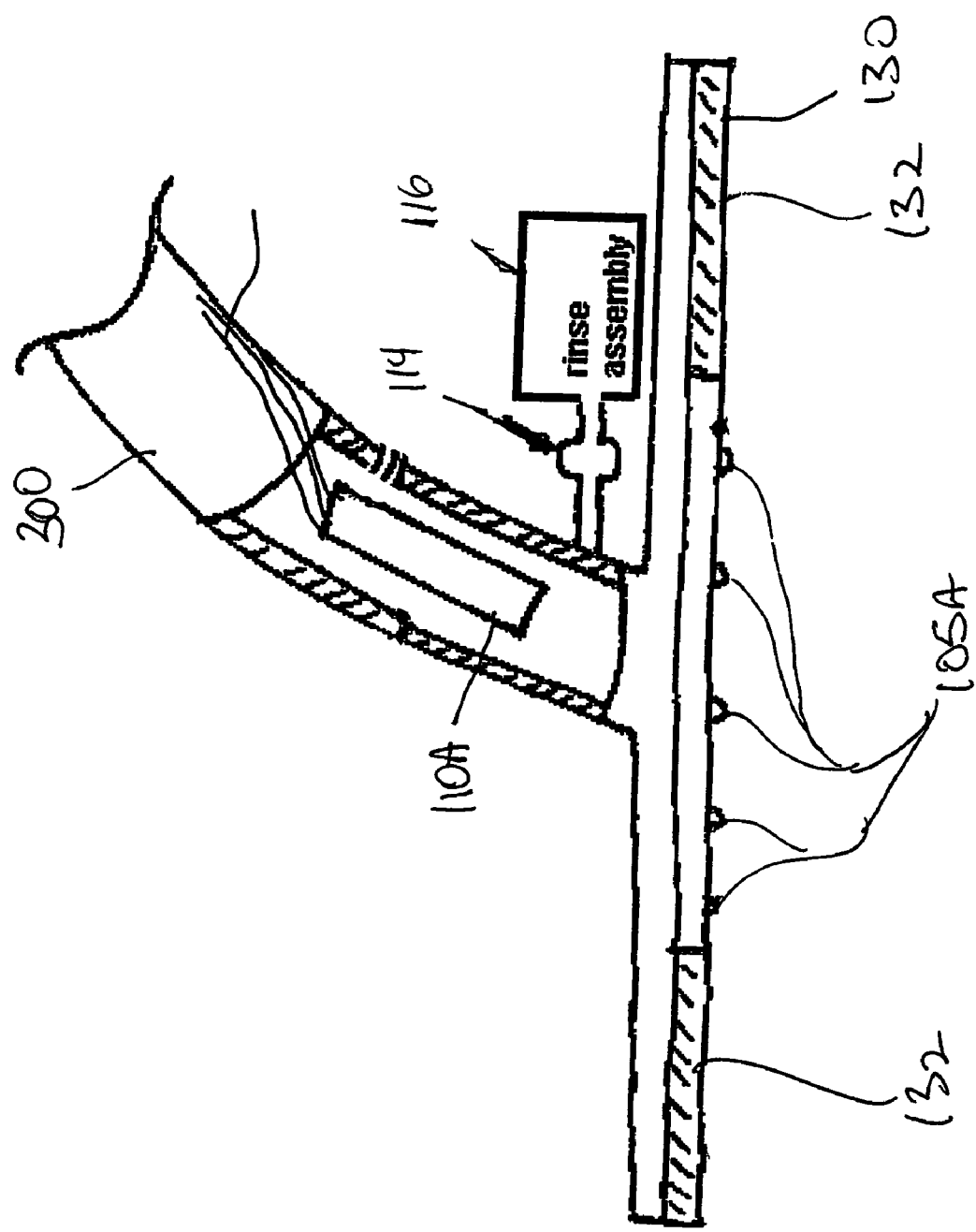

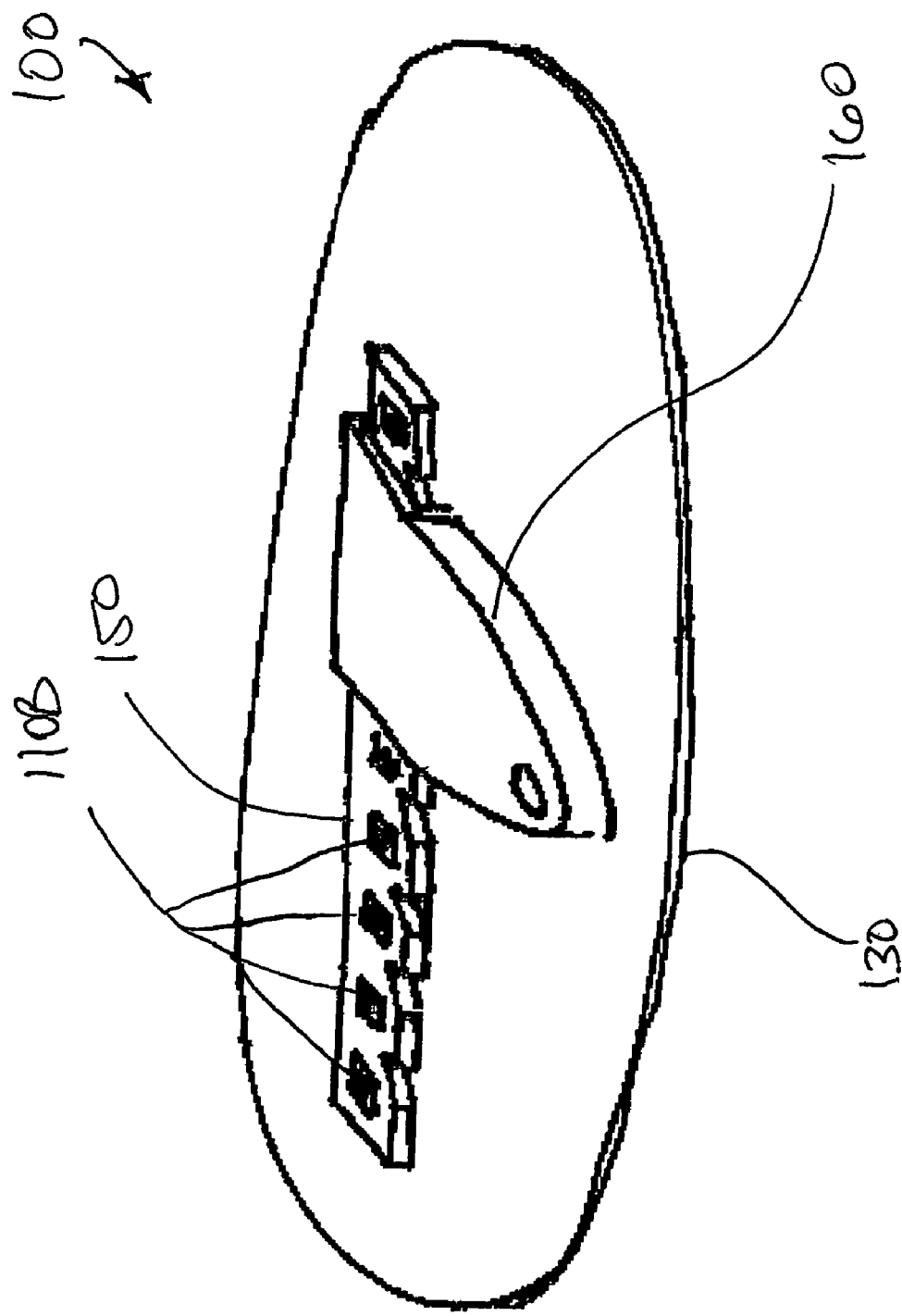

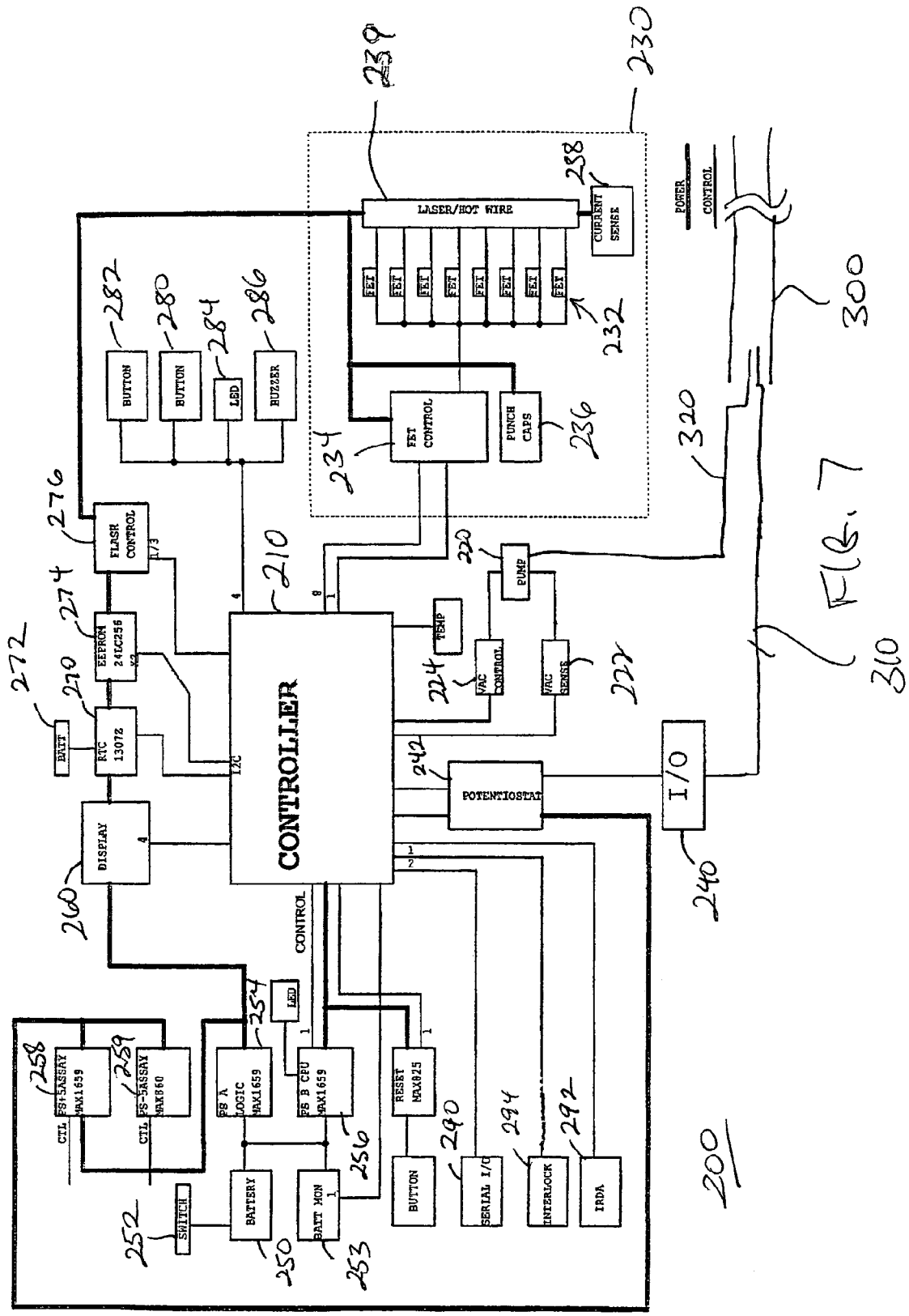

US 7,384,396 B2

SYSTEM AND METHOD FOR CONTINUOUS ANALYTE MONITORING

This application is a continuation of U.S. patent application Ser. No. 09/357,471 filed Jul. 20, 1999 now abandoned. Also, this application claims priority to U.S. Provisional Application No. 60/093,534 filed Jul. 21, 1998; U.S. Provisional Application No. 60/140,285 filed Jun. 18, 1999; and U.S. Provisional Application No. 60/140,252 filed Jun. 18, 1999. Each of these applications are hereby incorporated by reference.

BACKGROUND OF THE INVENTION

The present invention relates to analyte monitoring systems, and more particularly to a continuous analyte monitoring system wherein fluid is extracted from an organism and monitored outside of the organism to obtain a measurement of a characteristic of the fluid, such as analyte measurement.

Monitoring systems that sample and measure characteristics of fluids from an organism, such as a human, are well known. Many of these systems involve implanting sensors and related devices into the organism (such as under the skin) in order to obtain samples and make measurements of those samples. Even for short term implants, it has been shown that within the first several hours after implantation a rapid deposition of fibroblasts, macrophage plaques, fibrogen growth and other natural physiological encapsulation processes surround the implant and thereby impair, restrict, and modify, in a dynamic fashion, the free flow of the analytes of interest into the active sensor region of the implanted device. The typical method for compensating for these encapsulation effects involves calibrating the sensor against a conventional in vitro analysis method several times over the first few days. Further, once implanted, the sensors must be frequently calibrated, resulting in trauma to the implanted site and additional finger sticks to obtain the blood for calibration. The need to conduct multiple calibrations largely eliminates much of the advantages for many of the implanted continuous monitoring systems.

An additional restriction on the performance of the implantable sensors is that the internal environment is typically low in oxygen. This can limit the performance of many classes of reactive bio-sensors that invoke an analyte specific reaction which requires oxygen. One solution employed in some of the implants being developed is to use a restrictive diffusion membrane which limits the proportional amount of the analyte of interest which is allowed to reach the assay element, thereby extending the useable life of the implanted sensor in the oxygen lean internal environment. This compromise solution can have detrimental effects on response time, linearity of response to serum level changes in the analyte, and basic assay signal-to-noise ratio (SNR)

SUMMARY OF THE INVENTION

Briefly, according to one aspect, the present invention is directed to a system and method for extracting biological fluid from an organism and for continuously monitoring its characteristics. The system comprises a tissue interface device suitable for positioning on or about the surface of the biological membrane of the organism and a monitor and control unit coupled to the tissue interface device. The tissue interface device comprises a sensor positioned in a flow path of the fluid for continuously sensing a characteristic of the biological fluid as it is produced from one or more artificial openings formed in the tissue and in the flow path, and generates a sensor signal representative thereof. The monitor and control unit is coupled to the tissue interface device and receives the sensor signal to derive a measurement of a characteristic of the biological fluid on a continuous basis.

The present invention involves positioning the sensor ex vivo, on the surface of the organism or some distance away coupled via a fluid conducting member to the organism. Consequently, oxygen (if necessary) to support the sensor reaction is readily available, allowing for a simpler basic assay design, higher SNR, faster response, better linear tracking of the physiological changes in an analyte of interest, and longer life of the sensor. By keeping all of the foreign material of the sensor system outside of the body, the auto-immune driven encapsulation and rejection responses naturally occurring with any implanted device never begin.

Further, by avoiding actual penetration of the body to insert a sensor, a significant disadvantage of the implanted system is obviated by the system and method according to the present invention. Many people who would not consider using an implanted system become attractive candidates for this system. Also, the risks of infection present in prior art systems are dramatically reduced in connection with the present invention because neither sensor implantation is involved nor a membrane-breaching connection to an implanted sensor.

The above and other objects and advantages of the present invention will become more readily apparent when reference is made to the following description taken in conjunction with the accompanying drawings.

BRIEF DESCRIPTION OF THE DRAWINGS

FIGS. 3 and 4 are side views of suitable tissue interface devices through which micropores in the tissue are formed and fluid is collected and analyzed.

FIG. 5 is a side view showing the position of an amperometric sensor device with respect to a tissue interface device.

FIG. 6 is a perspective view of a tissue interface device featuring a cartridge containing a plurality of single use sensor devices.

FIG. 7 is a block diagram of the monitor and control unit.

DETAILED DESCRIPTION OF THE INVENTION

Definitions

Figure 1:
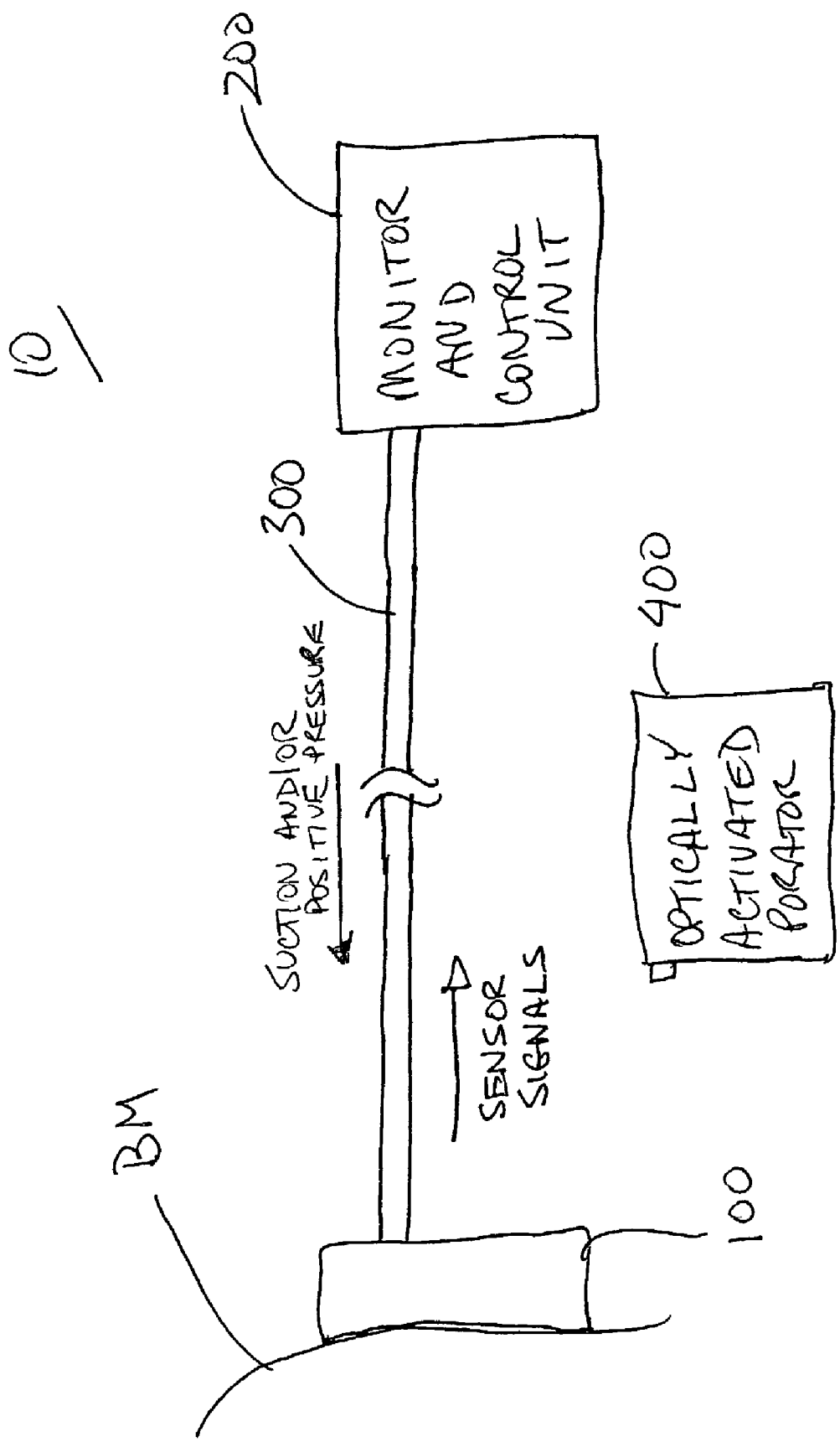
FIG. 1 is a block diagram generally showing the continuous analyte monitoring system according to the present invention.

As used herein, the term "biological membrane" means the structure separating one area of an organism from another area of the organism, such as a capillary wall, or the outer layer of an organism which separates the organism from its external environment, such as skin, buccal mucosa or other mucous membrane. The term "epithelial tissue,"

when used herein is mean to mean skin, mucosa and linings of the body cavities of an organism.

As used herein, the term "stratum corneum" means the outermost layer of the skin, consisting of from about 15 to about 20 layers of cells. The stratum corneum provides a barrier to the loss of water from inside the body to the external environment and from attack from the external environment to the interior of the body. The term "epidermis" means the metabolically active region of the skin. It is found just below the stratum corneum and is approximately 10 times as thick as the stratum corneum. The epidermis does not contain blood transport structures, i.e., capillaries. The term "dermis" means the region of skin approximately 10 times as thick as the epidermis and found just below the epidermis. The dermis contains large amounts of collagen, which provides structural integrity to the skin. The dermis contains a layer of small blood capillaries that provide oxygen and nutrients to the rest of the layers of skin.

As used herein, the term "tissue" means an aggregate of cells of a particular kind, together with their intercellular substance, that forms a structural material. At least one surface of the tissue is preferably, but not necessarily, accessible to electromagnetic radiation so that one embodiment of the invention can be carried out. The preferred tissue is the skin. Other tissues suitable for use with this invention include mucosal tissue and soft organs.

As used herein, the term "suction" or "pressure" relates to the relative pressure as compared to the internal pressure of the organism to which the system is interfaced. "Vacuum" is used synonymously with the term "suction."

As used herein, "ablation" refers to the process of controlled removal of a selected area of tissue from the surrounding tissue by kinetic energy released when the temperature of vaporizable substances in the selected area is rapidly elevated above the vaporization point thereby flash vaporizing some of the tissue in the selected area.

As used herein, the term "biological fluid" means blood serum, whole blood, interstitial fluid, lymph fluid, spinal fluid, plasma or any combination of these fluids. "Interstitial fluid" means the clear fluid that occupies the space between the cells in the body.

As used herein, "poration," "microporation," or any such similar term means the artificial formation of a small hole, opening or pore to a desired depth in or through a biological membrane, such as skin or mucous membrane, or the outer layer of an organism to lessen the barrier properties of this biological membrane to the passage of biological fluids, such as analytes from within the biological membrane or the passage of permeants or drugs from without the biological membrane into the body for selected purposes, or for certain medical or surgical procedures. The size of the hole or "micropore" so formed is approximately 1-1000 μm in diameter. It is to be understood that the term "micropore" is used in the singular form for simplicity, but that multiple openings or pores may be formed by the integrated device according to the present invention.

As used herein, "artificial opening" means any physical breach of the biological membrane of a suitable size for delivering or extraction fluid therethrough, including micropores.

As used herein, the term "integrated device" means a device suitable for forming small holes or micropores in tissue, collecting a biological fluid from the tissue (preferably through the micropores so created) and analyzing the biological fluid to determine a characteristic thereof.

As used herein, "sonic energy" refers to mechanical pressure waves with frequencies from 10 Hz to 1000 MHz.

The term "porating element" is meant to include any means of forming a micropore, hole or opening described above, including by thermal ablation, mechanically breaching the tissue by lancet or needle, and other known techniques. An example of a mechanical porating element is disclosed in commonly assigned published PCT application WO 9800193, entitled, "Multiple Mechanical Microporation Of Skin Or Mucosa." Another porating technique suitable for use in connection with this system is disclosed in commonly assigned U.S. application Ser. No. 09/353,130, entitled "Controlled Removal Of Biological Membrane By Pyrotechnic Charge For Transmembrane Transport," filed Jul. 14, 1999.

The term "heated probe" or "heat conducting element" means a probe, preferably solid phase, which is capable of being heated in response to the application of electrical, mechanical, sonic, magnetic, electromagnetic or optical energy thereto for achieving thermal ablation of the tissue. For simplicity, the probe is referred to as a "heated probe" or "heatable probe" which includes a probe in a heated or unheated state, but which is heatable.

The term "continuously" when used in connection with a continuous analyte monitoring system, means acting on an ongoing basis at a frequency or event rate that may vary depending on a particular application of the system. For example, the output of the sensor may be read on a periodic basis, such as every minute, several minutes, hour, several hours, etc. Moreover, at each reading event, the sensor output is optionally sampled multiple times, so as to obtain a plurality of readings relatively close in time, whereby an average or other adjustment of those multiple readings is made for determining a final reading that is displayed or logged.

Referring first to FIG. 1, the continuous analyte monitoring system according to the present invention is shown generally at 10. The system 10 comprises essentially three elements: a tissue interface device 100, a monitor and control unit 200 and a connector 300 that connects these two elements. Optional additional elements will also be referred to hereinafter. Generally, the function of the tissue interface device 100 is to attach to the surface of the tissue, make one or more artificial openings therein, collect fluid from the tissue and obtain a measurement of a characteristic of the fluid. The connector 300 provides mechanical, electrical and optionally optical communication between the monitor and control unit 200 and the tissue interface device 100. Alternatively, the connector 300 can be replaced by a wireless link by which the monitor and control unit 200 and the tissue interface device 100. In this case, the monitor and control unit 200 and the tissue interface device 100 would each have a suitable transceiver to communicate over the wireless link.

The monitor and control unit 200 continuously (or periodically) reads a signal representing the measured characteristic of the fluid, and in some applications, controls a suction force to the tissue interface device 100 to assist in the fluid collection and management process. Depending on the manner in which the artificial openings are formed in the tissue, an optional optically activated porator unit 400 may be provided. Also, the monitor and control unit 200 optionally includes the ability to apply a positive pressure to the biological membrane where the tissue interface device 100 is attached in order to press or squeeze the artificial openings to assist in extracting fluid from the tissue. The tissue interface device 100 ultimately produces an electrical signal that is indicative of a presence of concentration of an analyte. The electrical signal can be produced in several places. In one embodiment, the electrical signal is produced by a sensor at or near the site of fluid production. In another embodiment, optical reading means is provided in the monitor and control unit 200 to optically interrogate the sensor that is in contact with the fluid which changes its optical characteristics (e.g., color or reflectance intensity) in relation to a characteristic of the biological fluid, such as the presence of an analyte of interest). Alternatively, the optical reading means is incorporated in the tissue interface device 100 to convert an optically read signal to an electrical sensor signal that is coupled by electrical lead lines to the monitor and control unit 200.

Figure 2:
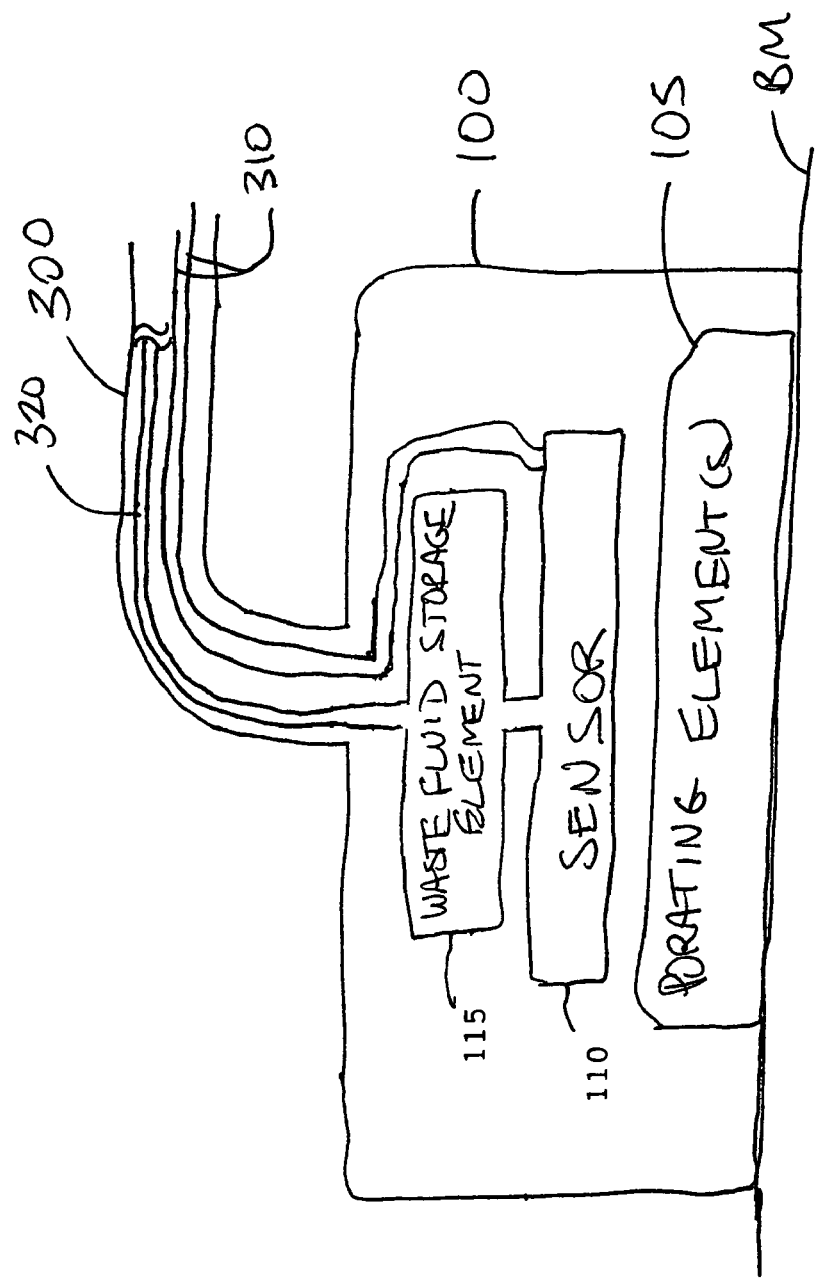
FIG. 2 is a schematic diagram of a tissue interface device for use in the system and method of the present invention.

Turning to FIG. 2, the tissue interface device 100 will be described. The tissue interface device 100 basically comprises a porating element(s) 105 and a sensor 110. The porating element(s) 105 may be one of several types, including a layer of optically sensitive material (photothermal material), one or more electrically heated elements, a mechanical porating element (such as a lancet or microlancet) that is either integral with the tissue interface device 100 or separate, or a chemical release mechanism that releases a quantity of chemical substance, such as a weak acid, that dissolves a sufficient amount of the tissue (geometrically confined by a mask). The specific type of porating element is not a central part of this invention. Commonly assigned U.S. Pat. No. 5,885,211 discloses examples of the electrically heated and optically heated porating elements.

The tissue interface device 100 is applied to the biological membrane (BM) preferably in an area which is less likely to sweat. Alternatively, the site of the BM where the tissue interface device 100 is to be applied (or the surface of the tissue interface device 100 that contacts the BM) is treated with an antiperspirant or other drug compound that reduces the production of perspiration locally. One such compound contains trace amounts of the botulism toxin, which limits the neurotransmitter acetylcholine from reaching the sweat glands. An example of such is the drug marketed as BOTOX™.

The sensor 110 may be one of any number of known types of analyte sensors, including an electrochemical biosensor, reactive enzyme based, reflectance, colorimetric, absorbance, fluorescence intensity or fluorescence lifetime based.

If the sensor 110 is a biosensor that is read electrically, the connector 300 comprises sensor leads 310 that electrically connect to the sensor 110 as is well known in the art. If the sensor 110 is a type that is read optically, then instead of sensor leads 310, the connector comprises an optical fiber through which a reading is made from an optical reading means in the monitor and control unit 200. Alternatively, as described above, an optical reading means comprising an optical source and detector is placed within the tissue interface device 100, and is controlled and read remotely from the monitor and control unit 200 via the electrical leads in the connector 300. In addition, the connector 300 comprises a tube 320 that connects suction or positive pressure to the tissue interface device 100. Suction applied over the artificial openings in the biological membrane is useful to continuously draw fluid from the tissue through across and into contact with the sensor 110. Positive pressure applied to the surrounding surface of the biological membrane is useful to induce fluid flow from the tissue into the tissue interface device 100. Methods for generating a positive pressure gradient in the surrounding tissues is an optional feature which is achieved by mechanical compression of the tissue structures, selective application of sonic energy as disclosed in the above-referenced U.S. Pat. No. 5,885,211, or the introduction into the surrounding tissues of an agent selected to produce a localized edematous response.

An optional waste fluid storage element 115 may be provided for some configurations of the tissue interface device to remove fluid sample from the sensor to ensure that subsequent samples of the fluid accurately reflect current analyte levels with the organism. More details about the waste fluid storage element are described in commonly assigned co-pending U.S. application Ser. No. 09/357,452, entitled "System And Method For Fluid Management In A Continuous Fluid Collection And Sensor Device," filed on even date.

Turning to FIG. 3, a tissue interface device 100 is shown comprising a plurality of electrically heated poration elements 105A disposed on a bottom surface of a tissue interface layer 130. A sensor 110 is disposed above the porating elements 105A. A portion of the tissue interface layer 130 may include adhesive 132 to facilitate attachment of the device 100 to the biological membrane. The adhesive 132 also is useful to form a pneumatic seal on the biological membrane to allow modulation of the pressure levels in those areas proximal the artificial openings. A top layer formed of oxygen permeable material is provided to which the connector 300 mates using known technology.

FIG. 3 shows a tissue interface device 100 having an layer of photothermal material as the porating element 105A. The porating element 105A is responsive to optical energy supplied either from an optical fiber contained in the connector 300, from a separate light source in an optically activated porator 400 (FIG. 1) or from a light source contained within the tissue interface device 100 itself. In any case, the photothermal material responds to the optical energy by heating up and delivering sufficient energy by conduction to the surface of the biological membrane to ablate the biological membrane and form one or more artificial openings therein.

More details on an integrated tissue poration and fluid harvesting device as shown in FIGS. 3 and 4 are disclosed in commonly assigned U.S. patent application Ser. No. 09/263,464, filed Mar. 5, 1999, entitled "Integrated Tissue Poration, Fluid Harvesting And Analysis Device and Method. Suitable compounds for the photothermal material are disclosed in commonly assigned PCT application No. PCT/US99/04990, filed Mar. 5, 1999, entitled Photothermal Structure for Biomedical Applications, And Method Therefor.

FIG. 5 illustrates a tissue interface device 100 that features an amperometric electrochemical biosensor shown at reference numeral 110A. This configuration also includes an optional rinse assembly 116 and a valve 114 to control the delivery of a flushing solution to the sensor. The flushing solution is useful to prevent deterioration of the sensor 110A and to purge the sensor of other fluid samples. More details on a mechanism for delivering a flushing solution to the sensor are provided in the aforementioned application filed on even date.

FIG. 6 illustrates still another form of a tissue interface device 10 featuring a plurality of one-time use sensors 110B arranged on a cartridge 150. A cartridge indexing mechanism 160 is provided to advance an unused sensor 110B into position for fluid sampling. When a new reading is to be obtained, a new unused sensor is indexed into position by the cartridge indexing mechanism 160 to be filled with the next fluid sample obtained. This design is compatible with all types of sensors, including electrochemical and calorimetric types that are currently used in the wide variety of personal glucose monitors in use, as well as many assay systems used in in-vitro clinical laboratory applications for analytes such as glucose and others.

Optional modifications to the tissue interface device 100 include those to enhance the flow of the fluid to the sensor 110 based on modified surface tension effects. For example, surfactant compounds are optionally applied to selected components of the tissue interface 100 to direct fluid flow to the sensor 110. Furthermore, a mesh may be provided in the tissue interface device 100 to wick interstitial fluid towards the sensor 110. The mesh is positioned and clamped between top and bottom layers of the device 100, or may be held in place by small thermal welds, glue, or mechanical spacers. The mesh acts by a surface tension mechanism to move the biological fluid to the sensor. Still further, a capillary channel may be formed between the top and bottom layers of the device 100, thereby creating surface tension effects to move the fluid to the sensor 110. All of the surface tension modifications are useful to facilitate the delivery of a bubble-free fluid sample to the sensor, thereby increasing the reliability and accuracy of the readings produced by the sensor.

The mesh may be treated with a surfactant compound as well. Further still, surfaces of the device 100 where it is desired that fluid not flow may be treated with hydrophobic compounds. The mesh will also displace volume in the device 100 to thereby reduce the volume of fluid needed for an adequate assay measurement. The technique of treating a wicking mesh layer with surfactants to transport a fluid to an assay sensor is known in the art. See, for example, U.S. Pat. No. 5,271,895 to McCroskey et al. Other examples of known uses of surfactant treated layers are disclosed in U.S. Pat. No. 3,992,158 to Przybylowicz et al., U.S. Pat. No. 4,050,898 to Goffe, deceased et al., U.S. Pat. No. 3,912,457 to Ogawa et al., U.S. Pat. No. 4,053,381 to Hamblen et al., U.S. Pat. No. 4,774,192 to Terminiello et al., and U.S. Pat. No. 4,839,296 to Kennedy et al.

The co-pending application filed on even date discloses a plurality of techniques for controlling fluid flow in the tissue interface device 100.

An indicator within the sensor may be provided to determine when the assay materials (enzymes, etc.) have been consumed and the sensor must be replaced or a new tissue interface device 100 installed. This is variable depending on the subject, the analyte being monitored, the levels of the analyte over time for that subject, the specific type of sensor utilized and other conditions.

The tissue interface device 100 is preferably flexible such that when attached to the subject's body in a selected location, the subject's natural muscle action acts to assist in keeping the collected fluid in motion across the sensor.

Before the tissue interface device 100 is applied to the BM of the tissue, the site on the BM where the artificial openings are to be formed may be treated with a ring-shaped area of a hydrophobic material, except for an area defining a capillary or wicking channel that abuts the site. The biological fluid will be directed into the channel and moved by capillary, wicking or vacuum into contact with the sensor.

Another possibility is to position the tissue interface device 100 such that the tissue interface layer 130 it is positioned very close to the BM but does not physically touch it, but is close enough that it contacts the drops of fluid coming out of the artificial openings in the BM. If the cover, so positioned, has a wicking, or capillary channel then the drops will combine and pool together on the surface of the cover before being draw to the assay. Alternatively, the sensor is placed on either side of the cover.

As a further level of protection, a sensor could be provided on the tissue interface layer 130 to detect water or sweat contamination of the poration sites. For example, an ion specific electrode is useful to detect a characteristic shift in sodium and/or potassium ion concentrations indicative of sweat contamination. Another way to detect such contamination is to use a sensor that senses a shift in pH, indicative of a situation in which an external contaminant, such as water, mixes with the collected fluid. Many analyte levels in the fluid are very stable and predictable, so that monitoring a "contamination test analyte" is useful to ensure that the analyte of interest is being measured and reported accurately. The sensor technologies useful for contamination monitoring are essentially the same as those described above for the sensor 110. Moreover, the sensor 110 shown in the figures and described above is optionally modified to measure a plurality of analytes, all or some of which are selected to produce outputs used to validate certain analyte measurements.

The materials used in fabricating the tissue interface device are preferably selected to match the water loss characteristics of the BM so that the damage repair mechanisms are delayed in operation. The adhesive-treated area, the vacuum (or pressure) seal ring (or area) and the poration/vacuum (or pressure) area could be designed to have this characteristic. GORETEX™ or other breathable waterproof fabrics are suitable to fabricate the tissue interface device 100 to control the water loss.

Turning to FIG. 7, the monitor and control unit 200 is shown in greater detail. The monitor and control unit 200 communicates with the tissue interface device 100 to continuously (or periodically) obtain readings from the tissue interface device 100 and controls the application of pressure (negative or positive) to the tissue interface device 100. The heart of the monitor and control unit 200 is a controller 210 that controls the overall operation of the system. The controller 210 maybe embodied by a low power microprocessor or other suitable processing device that is preferably programmable. An example are the Hitachi H8/3437 and H8/2148 controllers, the latter of which has an on-board flash memory capable of receiving programs stored thereto.

The monitor and control unit 200 comprises a pump 220, a vacuum sensor 222 and a vacuum controller 224. The pump 220 is connected by the tube 320 (contained inside or adjacent to the connector 300) to the tissue interface device 100. The controller 210 connects to both the vacuum sensor 222 and the vacuum controller 224. The vacuum sensor 222 monitors the level of negative pressure applied by the pump 220 and generates a signal that is fed back to the controller 210. The controller 210 periodically monitors the level of negative pressure applied by the pump 220 to issue control signals that are received by the vacuum controller 224 to control the level of pressure generated by the pump 220. The vacuum sensor 222 is located either at the tissue interface device 100 proximate the end of the tube 320, or in the tube 320 proximate the pump 220. Alternatively, vacuum sensors are positioned at both ends of the system and are calibrated to detect a seal leak by a measurable difference between readings obtained by the two vacuum sensors.

The electronics for controlling the poration elements in the tissue interface device 100 may be included within the monitor and control unit 200, or separate therefrom. The poration control circuit is shown at reference numeral 230 and comprises an array of electronically controllable switches, such as field effect transistors (FETs) 232, an FET control circuit 234, one or more capacitors 236 and a current sensor (such as a resistor) 238. The poration control circuit 230 controls the amount and pulse duration of current delivered to either one or more wire elements that are electrically heated, or to an optical source, such as a laser. This is represented at reference numeral 239 in FIG. 7.

The controller 210 reads the sensor signal(s) generated by the sensor 105 on the tissue interface device via the input/output (I/O) interface 240 and the lead lines shown at reference numeral 310. The I/O interface 240 couples to a potentiostat 242. The potentiostat 242 is essentially a current sensor. It is coupled to the output of the power supply circuits 258 and 259 and to the sensor signal generated by the sensor (of the variety that generates as output an electrical signal representing the measurement) in the tissue interface device to sense the mount of current of the electrical signal. The controller 210 then converts this current signal to a corresponding (digital) numeric value that is stored and/or displayed. Any compensation of adjustment of the measurement is made by the controller 210 using one or more adjustment algorithms (known in the art).

Power supply to the monitor and control unit 200 is by way of a battery 250. ON/OFF control is achieved through the switch 252. The voltage on the battery 250 is monitored by a battery monitoring circuit 253 that is coupled to the controller 210. The battery voltage is coupled to two power supply circuits 254 and 256. Power supply circuit 254 generates a first voltage that is used to power many of the other components of the monitor and control unit 200. Power supply circuit 256 generates a second voltage that is used to power the controller 210.

In addition, power supply circuits 258 and 259 are provided to generate reference voltages that are coupled to the sensor 105 via the lead lines 310 for purposes of electrically reading the sensor 105. In the event that reflectance-type or colorimetric sensors are employed that are optically read, optically reading means is provided for optically reading the sensor and converting the optical signal to an electrical sensor signal for processing by the controller 210. To this end, the optical reading means comprises light sources (such as LEDs) and detectors (such as photodiodes) that are optically coupled to the sensor in the tissue interface device 100. Alternatively, the optical reading means is incorporated at the tissue interface device 200 to convert an optical signal to an electrical sensor signal. Other optical devices, such as lenses, and mirrors are also optionally employed to optimize the optical readings so obtained. Alternatively, a fiber optic system may be employed that allows for placement of the source and detector components within the monitor and control unit 200, but linked to the sensor by optical fiber(s).

Other components of the monitor and control unit 200 are a display 260, real time clock (RTC) 270 and backup battery 272, electronically eraseable programmable read only memory (EEPROM) 274, and flash control circuit 276. The EEPROM 274 stores the digital measurement data values generated by the controller 210. It is the memory element to which the measurement data is logged, as explained hereinafter. The flash control circuit 276 is used to reprogram the controller 210 with updated or new software control and/or analysis procedures.

In order to enable a user to control and access information in the monitor and control unit 200, buttons 280 and 282 are provided, as well as a light emitted diode (LED) 284 and audible alarm device 286, such as a buzzer. In addition to the buzzer or in place thereof, a vibration alert device may be provided, such as those used in conventional wireless paging receivers.

To enable communication of information, such as programming and other information, the monitor and control unit 200 comprises a serial I/O port 290, infra-red demodulator (IRDA) 292 and an interlock circuit 294. The interlock circuit 294 verifies that the tissue interface device 100 is in proper position for forming the artificial openings and for harvesting fluid therefrom.

As explained above, the controller 210 controls the overall operations of the system preferably by way of a software program that is stored either in a memory in the controller 210 or a separate memory, such as EEPROM 274. Aside from controlling the formation of the artificial openings in the tissue, the operations of the controller 210 include (1) capturing, processing, display and logging (storing) sensor measurements on a continuous or periodic basis or on an on-demand basis; (2) providing user access to basic functions and data; (3) monitoring battery status; and (4) providing a diagnostic interface to the system.

In some cases, readings are made from the sensor in the tissue interface device 100 and a measurement is computed according to known processes (dependent on the type of sensor employed). The measurement is displayed on the display 260 and the data is logged for the EEPROM 274. In other cases, the measurement data is logged but not displayed. And in still other cases, the measurement data is dumped to the serial I/O 290 for use externally or for diagnosing the operation of the system. An optional feature of the system is to generate a control code that activates a wireless interface to alert a remote site of a developing or existing critical condition. The wireless interface is a cellular telephone link, paging system link or other radio link communication system. This is particularly useful in a hospital environment where the user is being monitored continuously in order to alert for assistance in the event of a hypoglycemic episode that the patient is otherwise unaware of.

Generally, the continuous monitoring method associated with the system is as follows. First, the tissue interface device 100 is placed in position on or about the biological membrane. Next, through one of the various poration techniques described above and in the reference patents, PCT publications and co-pending application, one or more artificial openings in the biological membrane are formed to facilitate the rapid access to biological fluid. Next, the fluid is induced to exit from the organism's body into the tissue interface device 100. This induction of fluid flux could be via a passive diffusion or leakage process, a suction enhanced process via negative pressure supplied from the monitor and control unit 200, a positive pressure enhanced process via positive pressure supplied from the monitor and control unit, a sonically enhanced process using the sonic energy techniques described in commonly assigned U.S. Pat. No. 5,885,211, an electric or magnetic field enhanced process, a chemically enhanced process wherein a quantity of a chemical flux enhancer is delivered into the one or more artificial openings to further reduce the fluid barrier functions of the biological membrane, the introduction of a compound into the artificial openings which reduces the viscosity of the fluid being collected thereby allowing more to flow within a given time, the introduction of a compound into the artificial openings that change the surface tension of the fluid being collected in a selected fashion to favor the fluid collection and/or manipulation within the harvesting apparatus, or any combination of these various flux enhancement techniques. Positive pressure excitations to the tissue surrounding the tissue interface device 100 may be modulated in the transverse direction as well as a longitudinal direction.

Figure 8:
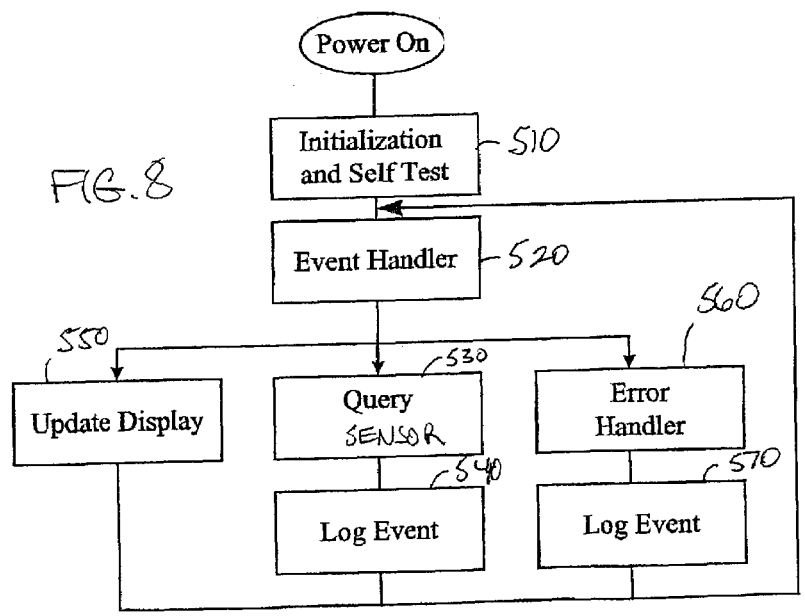
FIG. 8 is a flow chart depicting the basic monitoring processes according to the invention.

Turning to FIG. 8, the logic flow of software program of the controller 210 will be described in more detail. Once powered up, the controller 210 executes an initialization and self-test routine at step 510. Next, an event handler routine is executed at step 520 to determine the next action to take based on programmable event and timing parameters and other interrupts. For example, the frequency at which the sensor is to be read is a programmable parameter in the event handler routine. If the event handler routine determines that the sensor should be read, then in step 530 the sensor is read and a measurement is computed based on the sensor output (s) at that event. Next, in step 540, the measurement data is logged or stored in a memory if logging is to be made. Control returns to the event handler routine in step 520, where it is determined whether, for example, the measurement data just obtained from a sensor query event is to be displayed. If so, then the measurement data is coupled to the display to update the display in step 550. If the event handler 520 determines that an error has occurred, the error handler routine 560 is invoked to deal with the error, and the error event is logged in step 570.

The process of querying the sensor at step 530 is explained in greater detail. The controller 210 maintains the proper voltage bias to the sensor leads 3110 and reads the sensor output a number of times at a certain sampling rate to obtain a plurality of measurements. For example, the sensor output is read 10 times at 1 Hz. The measurement data for the plurality of readings is then checked by the controller 210 for any maximum deviation or "out-of-range" characteristics. Next, the plurality of readings is averaged. Then, the controller 210 applies a computation function (such as that derived from a stored look-up table) to the average reading value to determine a corresponding measurement value that is logged and/or displayed.

At each sensor reading event, the voltage on the battery 250 is monitored. The LED 284 may be energized to indicate a low battery condition when the battery voltage is determined to be below a first programmable threshold. Further, if it is determined that the battery voltage is below a second programmable threshold, an audible alarm, such as the buzzer 286, may be triggered and the system may be shut down. The battery voltage is also optionally logged with each sensor reading event in order to characterize battery performance. Based on the predictable behavior of the battery in the system, the logged battery data is useful to alert the user with an estimated time before replacement is mandatory. For example, the system is optionally configured to operate for a predetermined period of time of continuous application for each tissue interface device. Upon installation of a fresh tissue interface device the expected battery life calculation would be carried out and if it showed a low probability of being able to complete the next twelve hour cycle, the user could be warned at that time to replace or recharge the battery.

The diagnostic aspects of the controller include a power-up diagnostic that involves basic component activation and software verification. Such diagnostics include checking the RTC 270, pump 220, battery 250, and display 260.

Error events that may trigger activation of the error handling routine 560 include failure of the pump determined by the pressure falling outside a programmable range for more than a certain period of time, low battery voltage, inactive RTC 270, and invalid sensor measurements (discontinuity, out of range, noisy).

Other features of the monitor and control unit that may be useful for certain applications include a radio or infra red transmitter that generates a signal that includes the measurement data for transmission to a remote wireless receiver. This signal may be in the form of an outgoing messaging signal formatted in accordance with two-way paging or messaging standards or cellular telephone standards. The signal may be associated with an address of a particular recipient, such as a physician, nurse, parent, etc. The latter feature could be particularly useful with a young subject with diabetes who may be about to enter a hypoglycemic state, allowing the proper individual to initiate preventative steps prior to the individual entering a critical and more dangerous state.

Figure 9:
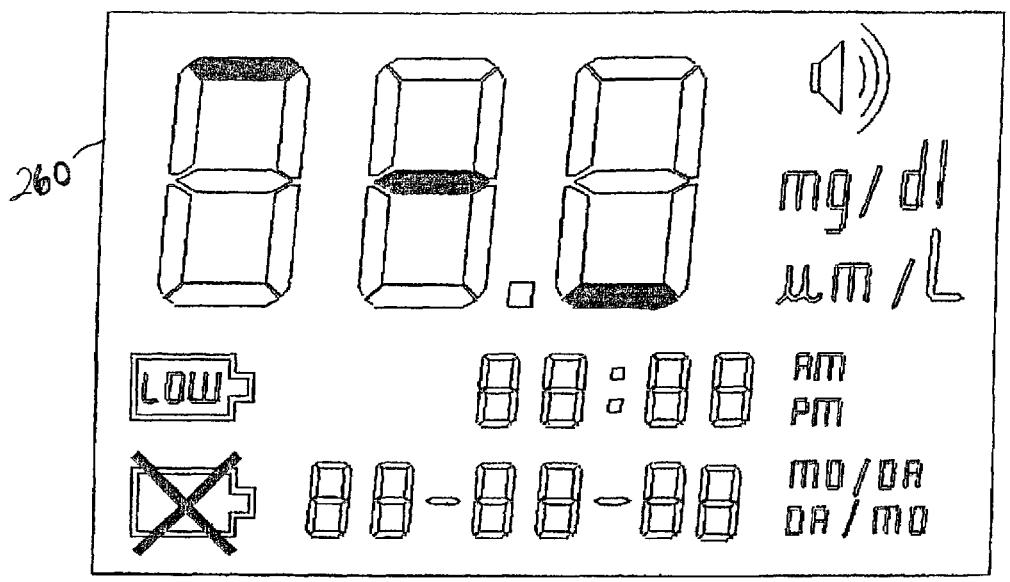
FIG. 9 is a diagram of a display device contained in the monitor and control unit shown in FIG. 7.

An example of a suitable display 260 is shown in FIG. 9. The display 260 may be an LCD or LED display, with display segments to display the analyte reading, such as a glucose reading, in mg/dl and µm/L, the time of the reading, and the date of the reading (month and day). In addition, the display 260 includes a display segment ("LOW") that is energized when a reading is determined to be lower than a certain threshold. A display segment is also provided that is energized when an audible alarm is activated. Alternatively, a synthesized voice output may be provided for the sight-impaired users, or for young children unable yet to read.

As an alternative to providing a supply of negative pressure and a separate pressure line, an inflatable bellows or pressure ring may be provided that is inflated when the user presses down on the tissue interface device 100 (much in the same manner as inflation adjustable shoes/boots) in order to apply pressure to the poration site and force fluid out. This would eliminate the need for a separate vacuum pump and vacuum hose.

The monitor and control unit 200 may be contained within a small, lightweight housing designed to be carried on the user's person for several hours, days or weeks at a time. This unit would then connect to the tissue interface device that contains the disposable portion of the system which provides the poration elements, the active element of the sensor, and some or all of the fluid harvesting and management systems. The control, display, meter, power supply, and other functions would be contained within the non-disposable monitor and control unit 200.

Alternatively, all of functions of the tissue interface device 100 and control and monitoring unit 200 may be integrated in a complete, single-use disposable monitoring system. In this case, size and cost constraints may favor omitting some of the more advanced features. This sort of system could be particularly useful for those subjects who may only need close monitoring of a selected analyte(s) for a relatively short period of time, such as a post-operative patient where a specific analyte may need to be monitored for several days immediately after the surgery.

The signal to trigger the measurement operation is optionally pre-programmed, triggered by an external command signal such as a query from a nurses station in a hospital environment, or on-demand by the subject himself/herself by pressing a manual "assay-now" button on the monitor and control unit 200. Similarly, this trigger may be sent from another system interfaced to the subject, such as an insulin pump wherein a dialogue between the sensor system, setup as a glucose sensor, could be used as a quasi-real-time control input for the modulation of the delivery of insulin. This same closed loop concept could be applied to many compounds and analytes such as dilantin, anti-psychotics, growth hormone, thyroid hormone, or the like, using the sensor system to monitor either the level of the substance being delivered, or the level of a separate analyte which is affected by the delivered substance, such as glucose. Insulin or calcium ion activity can be modified by the delivery of thyroid hormone.

The controller 210 is optionally programmed to generate alarm signals when measurements taken from the sensor fall outside certain ranges. For example, if a glucose reading falls outside a range, an alarm signal would be triggered to activate a visual or audible alarm with the nature of the alarm indicating a too low or too high reading. Alternatively, the controller 210 may be programmed to monitor a trend over a period of time, or readings below or above a threshold for a period of time before an alarm signal is issued. Further, the controller 210 may be programmed to execute additional readings if an alarm or impending alarm condition were detected. For example, if a user's glucose level was found to be 70 mg/dl, but the last reading, taken 1 hour ago was at 120, then the system could automatically trigger a follow-up reading or even a series of follow-ups, every five minutes to assess the trend and alert the user of the situation and the implications for a hypoglycemic episode potential within the next 10 to 30 minutes or so. Similarly, the controller 210 may be programmed to display trends to indicate whether the readings are rising, steady or falling with respect to prior readings. Further, the controller 210 is optionally programmed to compute first and/or second derivatives of readings from a series of several readings taken over time.

Figure 11:
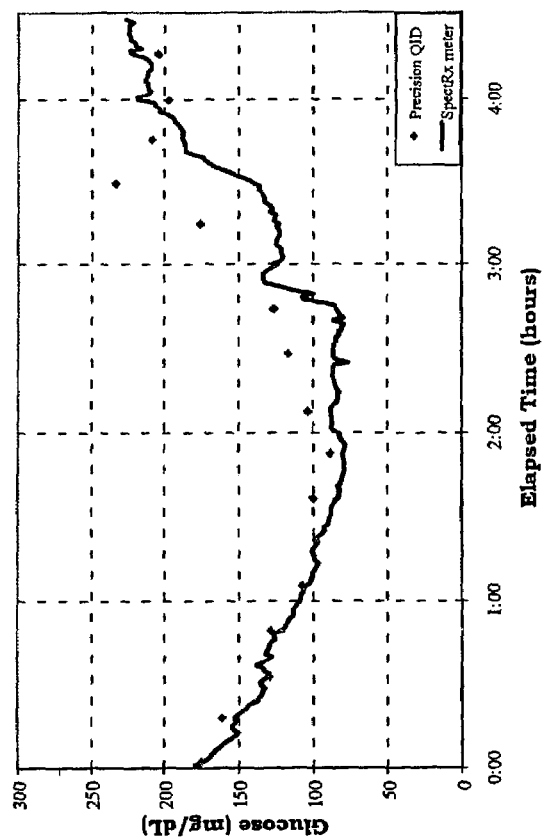
FIGS. 10 and 11 are graphical diagrams showing glucose measurement data taken with a continuous monitoring system according to the present invention.
Figure 10:
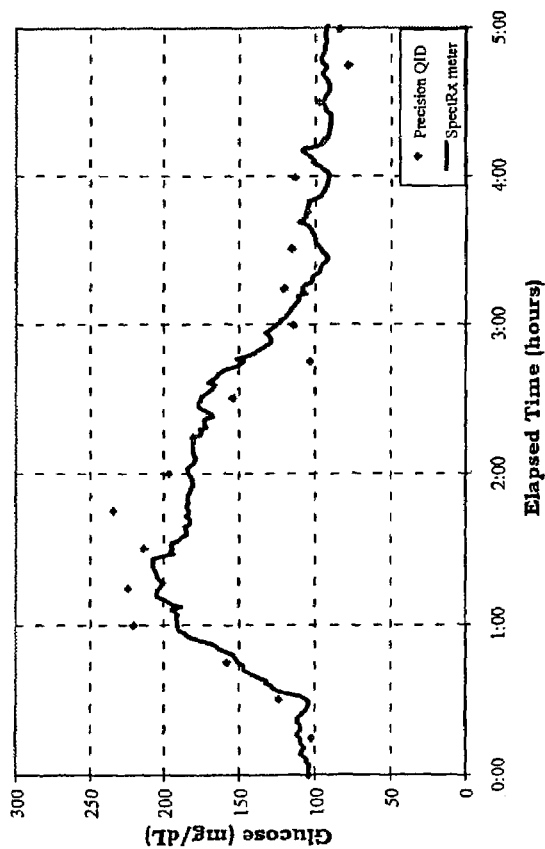

FIGS. 10 and 11 are graphical diagrams showing examples of glucose measurements made for a resting diabetic patient by a continuous monitoring system as compared to measurements made using a PRECISION QID™ blood glucose meter with blood obtained by a capillary finger-stick. The solid line in the figures is representative data taken by the continuous monitoring system and the data points in the figures correspond to the discrete meter readings with the PRECISION QID™ blood glucose meter. In FIG. 10, a glucose load was given at an elapsed time of 20 minutes. In FIG. 11, subcutaneous insulin was administered just prior to data collection, and a glucose load was administered at an elapsed time of 2:40. These figures also illustrate how alarm conditions can be programmed in the controller at certain glucose levels (above a programmable maximum or below a programmable minimum).

The system and method of the present invention achieve many advantages over prior art discrete and continuous monitoring systems. All of the advantages and convenience of an implantable continuous monitoring sensor system are retained, but by positioning the active sensor elements of the system installed ex vivo, on the surface of the organism's external biological membrane in a patch configuration, the ex vivo patch could be designed to last for hours, days, or even weeks, as needed.

In addition, by collecting fluid continuously, the microporation technology can easily overcome the limitations of the sample flux rate imposed on a discrete, single use assay system. Studies have shown that a given set of micropores can be maintained in an open fluid-producing condition for extended periods of time, particularly for the collection of interstitial fluid. In studies in which the site was purposefully left exposed to the air and no attempts were made to keep the pores from drying out, it was shown that even 14 hours after their formation, the pores could be induced to allow fluid outflux under by application of suction. In this study, it was noted that whereas the first 45 seconds of suction generally produced small amounts of fluid at the 14 hours point, subsequent 45-second applications showed the fluid flux rates increasing quickly to the peak levels exhibited earlier.

It has been observed that the artificial openings formed in the tissue eventually seal within a few days even if fluid is still being extracted from the openings. For example, with respect to skin, a clear proteinaceous film formed principally by the albumin and other proteins available in the ISF agglomerate and becoming denatured when exposed to the air. This is the first stage in the eventual dequamitization of the epidermis which results in the opening being totally eliminated over the next 7 to 14 days as the newly keratinized epidermal cells flatten and build up the stratum corneum in the pore site from the bottom up. A brief application of moisture to the proteinaceous film at the pore site after this barrier had formed was shown to quickly dissolve this layer of protein and allow the pores to open up once again and show the same fluid flux rates as when originally tested. Based on these results, the useful life of a porated site can be extended if it is kept protected from full exposure to the air and kept moist, so that the same set of openings could be used for many hours, days, or possibly weeks to access the fluid, and particularly interstitial fluid, from the body. Certain compounds routinely used as topical agents have been identified being useful to block or shut-off the natural repair/healing processes of the body which work to rebuild the porated portion of the epidermis. By incorporating one or more of these compounds into the tissue interface device 100 covering the pore site, further enhancement of the long term flux from the pores could be realized, with the added benefit of reducing some of the negative cosmetic aspects of the body's reaction to the poration process such as localized erethyma and edema in some cases.

The above description is intended by way of example only and is not intended to limit the present invention in any way except as set forth in the following claims.

What is claimed is:

1. A system for continuously monitoring a characteristic of a biological fluid extracted from an organism, comprising:
a tissue interface device suitable for positioning on or about a surface of a biological membrane of the organism, the tissue interface device comprising a sensor positioned in a flow path of the fluid for continuously sensing a characteristic of the biological fluid as it flows out from one or more artificial openings formed in the tissue and in the flow path; and
a monitor and control unit coupled to the tissue interface device that reads the sensor to derive a measurement of a characteristic of the biological fluid on a continuous basis and wherein said tissue interface device is capable of detecting a shift in pH, so that potential contamination of the biological fluid can be detected, and
further comprising a connector that connects the monitor and control unit to the tissue interface device, wherein the connector includes a tube extending the length thereof, wherein the monitor and control unit comprises a suction source that is coupled to the tube and provides suction to the tissue interface device so as to draw biological fluid from the one or more artificial openings and through the fluid collection and sensor device and wherein said tissue interface device further includes means for rinsing the sensor of biological fluid so that it may accurately assay fresh biological fluid.

2. The system of claim 1, wherein the sensor comprises an analyte sensor.

3. The system of claim 1, wherein the monitor and control unit comprises a controller that controls when readings are made from the sensor.

4. The system of claim 3, wherein the controller compares data obtained from the sensor with stored values and generates an alarm signal upon determining a deviation from the stored values.

5. The system of claim 4, and further comprising an alarm device that is responsive to the alarm signal to generate an audio and/or visual alarm.

6. The system of claim 1, and further comprising electrical lead lines coupling the sensor to the monitor and control unit, wherein the sensor in the tissue interface device generates an electrical sensor signal representing the characteristic of the biological fluid, the electrical lead lines coupling the electrical sensor signal to the monitor and control unit and wherein the sensor, upon detecting abnormal changes in pH, report same to the control unit, so that the user may determine if reported characteristics of the biological fluid are reliable.

7. The system of claim 1, wherein the sensor changes its optical characteristics in response to a characteristic of the biological fluid.

8. The system of claim 7, wherein the monitor and control unit comprises means for optically reading the sensor.

9. The system of claim 8, and further comprising at least one optical fiber coupled between the means for optically reading the sensor.

10. The system of claim 7, and further comprising electrical lead lines coupling the sensor to the monitor and control unit, wherein the tissue interface device comprises means to optically read the sensor and generate an electrical sensor signal representative thereof, the electrical lead lines coupling the electrical sensor signal to the monitor and control unit.

11. The system of claim 1, wherein the monitor and control unit comprises a controller that controls the level of the suction.

12. The system of claim 1, and further comprising a pressure sensor for measuring the suction applied to the tissue interface device, the pressure sensor generating as output a pressure signal representative thereof, wherein the monitor and control unit reads the pressure signal.

13. The system of claim 1, wherein the tissue interface device comprises one or more elements for forming one or more artificial openings in the biological membrane and for applying a sweat control substance to the biological membrane to reduce contamination by sweating.

14. The system of claim 1, wherein the tissue interface device is attached to the surface of the biological membrane for a period of time to continuously collect biological fluid and sense characteristics thereof during the period of time, while periodically flushing the sensor of biological fluid.

15. The system of claim 1, and further comprising one or more electrical conductors that are connected between the tissue interface device and the monitor and control unit to communicate signals therebetween.

16. The system of claim 1, wherein the monitor and control unit is contained within a body wearable or attachable housing.

17. The system of claim 1, wherein the monitor and control unit comprises a memory coupled to the controller for storing data obtained from the sensor on a programmable periodic basis.

18. A system for continuously monitoring a characteristic of a biological fluid extracted from an organism, comprising:
 a tissue interface device suitable for positioning on or about a surface of a biological membrane of the organism, the tissue interface device comprising a sensor positioned in a flow path of the fluid for continuously sensing a characteristic of the biological fluid as it flows out from one or more artificial openings formed in the tissue and in the flow path; and
 a monitor and control unit coupled to the tissue interface device that reads the sensor to derive a measurement of a characteristic of the biological fluid on a continuous basis and wherein said tissue interface device is capable of detecting a shift in pH, so that potential contamination of the biological fluid can be detected, and
 further comprising a connector that connects the monitor and control unit to the tissue interface device, wherein the connector includes a tube extending the length thereof, wherein the monitor and control unit comprises a suction source that is coupled to the tube and provides suction to the tissue interface device so as to draw biological fluid from the one or more artificial openings and through the fluid collection and sensor device and wherein said tissue interface device further includes means for rinsing the sensor of biological fluid so that it may accurately assay fresh biological fluid and further including a sweat control substance that functions by incapacitating the sweat glands.

19. The system of claim 18, wherein an optical energy source is contained within the monitor and control unit, and further comprising an optical fiber that couples a beam of optical energy to an optically absorbent material on the tissue interface device.

20. The system of claim 18, wherein the monitor and control unit comprises a display coupled to the controller that displays measurement data.

* * * * *